United States Patent
Harris et al.

(10) Patent No.: US 6,787,163 B2
(45) Date of Patent: Sep. 7, 2004

(54) THERAPEUTIC TREATMENT FOR BLOOD SUGAR REGULATION

(76) Inventors: Dennis H. Harris, 4015 N. 40th Pl., Phoenix, AZ (US) 85018; Robert C. Martin, 10488 N. 119th Pl., Scottsdale, AZ (US) 85259

( * ) Notice: Subject to any disclaimer, the term of this patent is extended or adjusted under 35 U.S.C. 154(b) by 0 days.

(21) Appl. No.: 10/349,357

(22) Filed: Jan. 21, 2003

(65) Prior Publication Data

US 2004/0142045 A1 Jul. 22, 2004

(51) Int. Cl.⁷ ............................................. A61K 35/78
(52) U.S. Cl. ..................................................... 424/725
(58) Field of Search ......................................... 424/725

(56) References Cited

U.S. PATENT DOCUMENTS 6,271,254 B1 * 8/2001 Ulrich et al.
6,277,842 B1 * 8/2001 Carthron
6,448,287 B1 * 9/2002 Casciari et al.
2002/0143039 A1 * 10/2002 Krajcik et al.

FOREIGN PATENT DOCUMENTS

| HU | 34125 | * | 2/1985 |
| HU | 40571 | * | 1/1987 |
| HU | 43248 | * | 10/1987 |
| JP | 02002145772 | * | 5/2002 |

* cited by examiner

*Primary Examiner*—Michael Meller
(74) *Attorney, Agent, or Firm*—Joseph W. Mott

(57) ABSTRACT

A nutritional supplement formulation for the enhancement of blood sugar regulation, prevention and treatment of insulin resistance, prevention and treatment of dysinulinemia, prevention and treatment of Syndrome X, and reduction of diabetic complications is disclosed. The formulation combines herbs, minerals and vitamins known to reduce insulin resistance with herbs, minerals and vitamins known to reduce blood sugar levels.

1 Claim, No Drawings

US 6,787,163 B2

THERAPEUTIC TREATMENT FOR BLOOD SUGAR REGULATION

STATEMENT OF INVENTION

An oral nutritional supplement formulation for the enhancement of blood sugar regulation, prevention and treatment of insulin resistance prevention and treatment of hypoinsulinemia and hyperinsulinemia, prevention and treatment of Syndrome X, improvement of energy levels, reduction of blood sugar swings, reduction of blood sugar levels, weight management, and delay In the onset and decrease in the severity of diabetic complications. This formulation may be used with or without additional ingredients to treat and/or prevent blood sugar dysregulation.

BACKGROUND OF THE INVENTION

According to the American Diabetic Association, there are approximately 20,000,000 Americans today that have been diagnosed with diabetes. Impaired glucose tolerance, a precursor to diabetes, affects an additional 20–30,000,000 individuals. It is currently estimated that 2,200 new cases of diabetes are being diagnosed daily in the United States. Type 2 diabetes, previously called "adult onset diabetes", is an extremely common problem with potentially serious consequences. Individuals who suffer from Type 2 diabetes have significantly increased risks of heart attack, hypertension, stroke, peripheral vascular disease, hyperlipidemia, kidney failure, cataracts, retinal damage and obesity, among others. It is now estimated that at least one third of all Americans have a genetic tendency to develop the disease.

Diabetes has been rising at a startling rate-more than 30% in the past decade. As many as 95% of all diabetics are classified as Type 2, a disease that, until several years ago, primarily occurred in overweight adults over 45 years of age. Today, however, the disease does not discriminate. Women and men of all races and ethnic groups, along with children and adolescents, are developing Type 2 diabetes. In Type 2 diabetes, the pancreas may be producing insulin, but the body has developed insulin resistance, which interferes with the ability of insulin to metabolize the sugar. Approximately 5% of all those affected have Type 1 diabetes, previously called "juvenile diabetes", in which the beta cells of the pancreas have been destroyed and therefore fail to produce insulin. The majority of those with Type 1 diabetes develop the disease before age 30.

Although diabetes is believed to have multiple etiologies including, but not limited to, genetics, diet, exercise, sleep, caloric intake, trauma, infection, stress, drug ingestion, autoimmune reactions and life style factors, the following will focus primarily on the efficacy and use of nutritional/nutraceutical agents for the management of blood sugar dysregulation. The object of the present invention is to provide a unique combination of vitamins, minerals, herbs and other nutritional/nutraceutical ingredients that will aid in the management of hyperglycemia and blood sugar dysregulation of any type, as well as aid in the improvement of cellular sensitivity to insulin.

BRIEF SUMMARY OF THE INVENTION

The present invention preserves the advantages of oral nutritional/nutraceutical ingredients In the management of blood sugar dysregulation, Type 2 diabetes, dysinsulinemia, Syndrome X and insulin resistance. In addition, it provides new advantages not found in the currently available or formulations and overcomes many disadvantages of such currently available formulas.

This invention involves the novel and unique combination of nutritional/nutraceutical ingredients to be taken as an oral supplement for enhancing blood sugar regulation and controlling hyperglycemia, hypoinsulinemia, hyperinsulinemia and aspects of Syndrome X.

The composition may further comprise a delivery form for these components, such as powder, liquid, spray, tablet, caplet, or aerosol. Administration of the composition is anticipated to typically be via the oral route, but other forms of the composition may be delivered via the intramuscular, subcutaneous, intravenous, intranasal or sublingual routes. The invention may also Include ancillary ingredients such as coloring agents, excipients, binders, release agents and flavorings, among others, as commonly known in the art.

DETAILED DESCRIPTION OF THE INVENTION

One of the most universal changes with age is a progressive loss of glucose tolerance. When this loss of glucose tolerance becomes pronounced, it is diagnosed as diabetes. The most likely cause of this loss of glucose tolerance with age is a progressive loss of insulin sensitivity by hypothalamic receptors and a decreased response to glucose and insulin by the peripheral tissue. Insulin resistance is the central metabolic defect In a cluster of disorders now referred to as Syndrome X. This cluster of diseases includes Type 2 diabetes meliltus and hyperinsulinemia.

A very large study recently completed by the American Diabetes Association indicated that the onset of the major complications of diabetes, retinopathy, nephropathy and neuropathy, could be significantly delayed and the severity of these complications minimized by utilizing very tight glucose control. This involves decreasing the gap between the level of hyperglycemia and normal glucose levels. These findings have been confirmed in a parallel study in the United Kingdom. Unfortunately, even the drugs most commonly used for the treatment of Type 2 diabetes do not accomplish this task in the majority of patients.

Many studies have been performed on various naturally occurring herbs and other compounds, demonstrating their ability to lower blood sugars. While many of these compounds decrease the blood glucose level by stimulating the pancreas to produce more insulin, one particular herb, Goat's Rue or French Lilac, chemically known as guianidine, is particularly effective in reducing the blood glucose level utilizing a different mechanism. This herb actually decreases the cellular resistance to insulin, allowing the cells to utilize the insulin more efficiently in metabolizing glucose. It also decreases the absorption of glucose from the small intestine. It reduces the formation of glucose in the liver, and it increases the uptake and utilization of glucose in the fat and muscle cells throughout the body. Non-insulin dependent diabetics are able to better maintain blood glucose levels closer to the normal range, while insulin dependent diabetics are often able to reduce their insulin dosage and more easily maintain stable levels of the blood glucose.I This invention is a unique combination of French lilac and other natural compounds to provide a method of safely balancing the blood glucose levels in a way that minimizes the gap between the higher and lower measurements of blood glucose while providing mild pancreatic stimulation to bring the blood insulin levels closer to normal.

The preferred embodiment is as follows, listed by amount:

| THERAPEUTIC TREATMENT FOR BLOOD SUGAR REGULATION | |
|---|---|
| Ingredient | Amount |
| French Lilac/Goat's Rue | 1-1000 mg |
| Cinnamon | 1-1000 mg |
| American Ginseng | 1-1000 mg |
| Bitter Melon | 1-1000 mg |
| Gymnema Sylvestre | 1-1000 mg |
| Garlic | 1-1000 mg |
| Alpha Lipoic Acid | 1-1000 mg |
| 5-Hydroxytryptophane | 1-500 mg |
| Diethylaminoethanol | 1-1000 mg |
| Vitamin B Complex | 1-500 mg |
| GTF Chromium | 1-1000 mcg |
| Vanadyl Sulfate | 1-100 mg |
| Magnesium | 1-1000 mg |
| Potassium | 1-500 mg |
| Manganese | 1-100 mg |
| Zinc | 1-200 mg |
| Copper | 1-1000 mcg |

A specific preferred embodiment shown to be effective comprises 100 mg French Lilac/Goat's Rue, 50 mg cinnamon, 100 mg American ginseng, 100 mg bitter melon, 200 mg Gymnema Sylvestre, 25 mg Garlic, 15 mg Alpha Lipoic Acid, 5 mg 5-Hydroxytryptophane, 12.5 mg Diethylaminoethanol, 40 mg Vitamin B Complex, 200 mcg GTF Chromium, 4 mg of 19% Vanadyl Sulfate, 100 mg of 56% magnesium oxide, 99 mg of 20% potassium citrate, 2.5 mg of 18% manganese ascorbate, 12.5 mg of 80% zinc oxide, and 0.5 mg of 10% copper chelate.

In addition to the effects of French Lilac, scientists at the US Agricultural Research Services' nutrition laboratories in Beltsville, Md., found that an extract of cinnamon can actually revitilize the body's ability to be far more responsive to insulin in peripheral tissues, e.g. adipose and muscle tissue. In fact, in laboratory experiments, glucose processing was increased by up to 20 times. The chemical responsible is called methylhydroxy chalcone polymer. Experiments on mice found that abnormally high glucose concentrations fell dramatically when given this cinnamon derivative.

A study published in the Archives of Internal Medicine, a publication of the American Medical Association, showed that in non-diabetics, using American ginseng prior to a "glucose challenge" significantly reduced blood sugar. For diabetics, blood sugar levels were lowered whether the ginseng was taken before or during the meal. In another study published in Diabetic Care, ginseng therapy decreased blood glucose in non-insulin dependent diabetic patients.

The oral administration of Bitter melon has shown good results in clinical trials with patients with Type 2 diabetes. Bitter melon is composed of several compounds with confirmed anti-diabetic properties.

Two animal studies found Gymnema sylvestre extracts doubled the number of insulin secreting beta cells in the pancreas and returned the blood sugar almost to normal. Gynema sylvestre also increases the activity of enzymes responsible for glucose uptake and utilization. Several other animal studies have also confirmed the blood sugar lowering effects of this compound.

Onions and garlic have demonstrated blood sugar lowering action in several studies. The active principles are believed to be sulfur-containing compounds—allyl propyl disulphide (APDS) in onions and diallyl disulphide oxide in garlic—although other constituents may play a role as well. Experimental and clinical evidence suggests that APDS lowers glucose levels by competing with insulin for insulin-inactivating sites in the liver.

Alpha lipoic acid has been shown to improve insulin regulated glucose disposal in animal models of insulin resistance and Type 2 diabetic patients. The data shows that Alpha lipoic acid mimics insulin action by activating the signaling cascade at or before the level of phosphatidyl-inositol-3-kinase. In another study reported in Diabetes 2001, Alpha lipoic acid was shown to lower blood glucose levels in diabetic animals. In addition, it enhanced glucose uptake into the peripheral tissues.

A role for Vitamin B2 (thiamine) in cellular glucose transport has been indicated in the literature. Vitamin B2 plays an important part in the regulation of glucose metabolism and pancreatic beta cell functioning.

Vitamin B3 (niacin nicotinamide/nicotinic acid) is also a significant factor in glucose metabolism. Niacin contains enzymes which play an important role in energy production and carbohydrate metabolism. Nicotinic acid is an essential component of the glucose tolerance factor, making it a key nutrient for treating hypoglycemia and diabetes. Nicotinamide has been shown to prevent the development of diabetes in experimental animals.

Biotin supplementation has been shown to enhance insulin sensitivity and increase the activity of glucokinase the enzyme responsible for the first step in the utilization of glucose by the liver. In one study, biotin supplementation resulted in significant reduction of fasting blood glucose levels and improvement in blood glucose control in insulin dependent diabetes melitus. In another study of non-insulin dependent diabetics, similar effects were noted.

There is evidence that chromium deficiency is more common in the United States than previously suspected. A chromium deficiency may be a significant underlying factor in the large number of Americans suffering from diabetes, hypoglycemia and obesity. Reversing chromium deficiency by supplementing the diet with chromium has also been demonstrated to lower body weight while increasing lean muscle mass. All of the effects of chromium appear to be due to increased insulin sensitivity. Clinical studies in diabetics have shown that supplementing the diet with chromium can decrease fasting blood glucose levels, improve glucose tolerance and lower insulin levels.

Human studies involving vanadium have all been performed utilizing subjects who have Type 2 diabetes, or non-insulin dependent diabetes melitus (NIDDM). Vanadium was shown to improve both hepatic and skeletal muscle insulin sensitivity in NIDDM subjects in part by enhancing insulin's inhibitory effect on lipolysis. These data suggest that vanadyl sulfate may improve a defect in insulin signaling specific to NIDDM. Another study demonstrated modest reductions of fasting blood glucose and hepatic insulin resistance as a result of supplementing with vanadyl sulfate.

Zinc is involved in virtually all aspects of insulin metabolism-synthesis, secretion and utilization. Zinc also has a protective effect against beta cell destruction. Diabetics typically excrete excessive amounts of zinc in the urine, producing a deficit which makes supplementation mandatory for the maintenance of good health. This supplementation has been shown to improve insulin levels in both Type 1 and Type 2 diabetics. Additionally, zinc has an antihyperglycemic effect. Zinc can also Influence the production of leptin, a satiety factor that reduces appetite and blood sugar level.

Magnesium is involved in several areas of glucose metabolism, and there is considerable evidence that diabetics need supplemental magnesium. Hypomagnesemia occurs in approximately one third of patients with Type 2 diabetes. Several studies have suggested an association between magnesium depletion and insulin resistance and/or reduction of insulin secretion in these cases.

There are several reasons why diabetics should receive additional potassium. Supplementation of potassium yields improved insulin sensitivity, responsiveness and secretion.

Copper is a component, along with zinc, of one type of superoxide dismutase (copper/zinc/SOD). Deficiency may result in significant susceptability to free radical damage. Free radicals are thought to be involved in most degenerative diseases, including Type 2 diabetes.

Manganese is a cofactor in many enzyme systems involved in blood sugar control, energy metabolism and thyroid hormone function. In guinea pigs, a manganese deficiency results in diabetes and the frequent birth of offspring who develop pancreatic abnormalities or have no pancreas at all. Diabetics have been shown to have only one half of the level of manganese compared to non-diabetics.

There is evidence to suggest that the usage of tryptophan restores hypothalamic sensitivity. Loss of hypothalamic sensitivity may give rise to reduced glucose tolerance and loss of insulin sensitivity.

Many alterations may be made by those having ordinary skill in the art without departing from the spirit and scope of the invention. Although the present invention has been described with reference to preferred embodiments, numerous modifications and variations can be made, some of which are described herein, and the results will still come within the scope of the invention. Said modifications and variations were put forth only by way of example and not as a limitation to the scope of our invention as set forth in the objects thereof and in the appended claims.

We claim:

1. A combination of natural components for use in the treatment of abnormal sugar metabolism comprising about 100 mg French Lilac/Goat's Rue, about 50 mg cinnamon, about 100 mg American ginseng, about 100 mg bitter melon, about 200 mg Gymnema Sylvestre, about 25 mg Garlic, about 15 mg Alpha Lipoic Acid, about 5 mg 5-Hydroxytryptophane, about 12.5 mg Diethylaminoethanol, about 40 mg Vitamin B Complex, about 200 mcg GTF Chromium, about 4 mg of 19% Vanadyl Sulfate, about 100 mg of 56% magnesium oxide, about 99 mg of 20% potassium citrate, about 2.5 mg of 18% manganese ascorbate, about 12.5 mg of 80% zinc oxide, and about 0.5 mg of 10% copper chelate.

* * * * *